United States Patent [19]

Neuzillet et al.

[11] Patent Number: 4,653,912
[45] Date of Patent: Mar. 31, 1987

[54] INSPECTION BOOTH FOR SUBSTRATES COATED WITH A THIN FILM

[75] Inventors: Desire Neuzillet, Chalon sur Saone; Francois De Toytot, Thourotte, both of France

[73] Assignee: Saint-Gobain Vitrage, Courbevoie, France

[21] Appl. No.: 777,466

[22] Filed: Sep. 18, 1985

[30] Foreign Application Priority Data

Sep. 19, 1984 [FR] France ................................ 84 14344

[51] Int. Cl.[4] ..................... G01N 21/01; G01N 21/29; G01N 21/89
[52] U.S. Cl. .................................................. 356/237
[58] Field of Search .............................. 356/237–239, 356/30, 432, 433, 445, 446, 448; 350/276 R, 284

[56] References Cited

U.S. PATENT DOCUMENTS 1,956,165 4/1934 Boggs et al. .................... 356/239
2,015,730 10/1935 Rosin et al. ..................... 356/237

Primary Examiner—Eugene R. LaRoche
Assistant Examiner—David Mis
Attorney, Agent, or Firm—Pennie & Edmonds

[57] ABSTRACT

Apparatus is disclosed for examining thin layers deposited on a glass substrate of the plate or strip type under a lighting environment similar to that of outside daylight. The apparatus comprises an inspection booth having a station for observing the surface to be checked and a curved arch above the station to reflect light onto the surface to be observed. The curved arch is uniformly illuminated, has a neutral color, and is curved in an approximately concave manner to direct the light uniformly onto the surface to be examined. This booth permits quality control of layers such as metallic oxides deposited on glass substrates.

14 Claims, 1 Drawing Figure

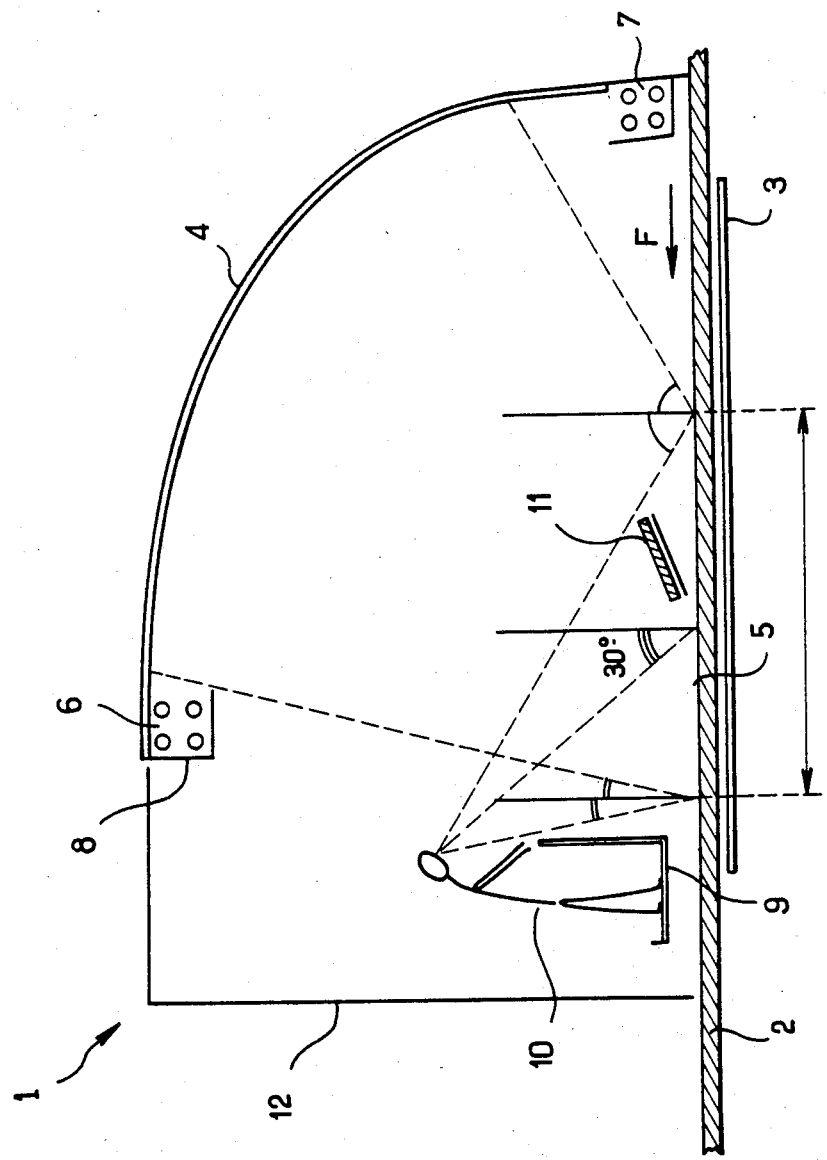

INSPECTION BOOTH FOR SUBSTRATES COATED WITH A THIN FILM

BACKGROUND OF THE INVENTION

The present invention relates to an apparatus for examining a surface of a substrate in a lighting environment similiar to that of outside daylight. A specific embodiment of the invention is implemented in an apparatus for examining a thin layer of metallic oxide such as an $SnO_2$ based substance deposited on a glass plate or strip. The thickness and uniformity of the layer is very important since variations in thickness tend to quickly induce variations in tint and other undesirable effects.

Evaluation of the quality of these layers is performed partly by visual examination of the layers, especially in the case of non-uniform layer thickness which gives rise to undesirable tint characteristics visible to an observer in daylight.

The most accurate and reliable observations of these layers are made in outside daylight. Observations in the workshop of these layers inevitably include reflection from surrounding superstructures which tend to place the glass in a false light and thereby make proper examination difficult. However, it is desirable to examine the coated glass at the place of production, before being brought to outside daylight, so that possible production problems may be immediately remedied in case of unsatisfactory quality. In addition, such an immediate observation is advantageous in that there exists no dependence on the daily or seasonal variations of illumination of the sky.

SUMMARY OF THE INVENTION

An object of the present invention is an inspection booth for examining substrates coated with a thin layer of material in an environment approximating outdoor daylight. This is accomplished through the use of an approximately concave surface, or arch, surrounding the substrate from which light is reflected onto the substrate to be examined. Such a method to reflect light incident to the arch from a plurality of light sources serves to approximate light from an overcast sky which is well known to be very discriminating in the detection of defects in the layers. Such defects may include heterogeneity of tint and iridescences.

In a preferred embodiment of the apparatus, the inspection booth is equipped with an approximately concave surface or arch which is mounted above the substrate to be inspected. This concave surface is continuous and curved with a radius that is constant or varying in a monotonic and continuous manner. The surface is covered with an opaque, mat-type, neutral-colored coating approximately equivalent in reflective properties to the illuminant $D_{65}$ of the ICI (International Commission on Illumination). The concave surface is illuminated indirectly and uniformly by light sources with properties similar to the illuminant $D_{65}$, preferably at the ends of the concave surface. The booth is also equipped with an observation station approximately opposite the concave surface so that an observer located at this station may inspect the substrate which is placed below the observer at a distance approximately between the concave surface and the observer so as to be uniformly illuminated by the concave surface. The booth is situated so as to provide the observer with a view of the substrate at an average angle of incidence on the order of 30°.

Immobile substrates may be inspected, as well as substrates in linear motion with respect to the observer. To facilitate such inspection, the arch is of such a size that it reflects over a length on the order of three meters opposite the observer.

BRIEF DESCRIPTION OF THE DRAWING

These and other objects, features and advantages of the invention will become more readily apparent with reference to the following description of a preferred embodiment of the invention in which the drawing is a graphical representation of an illustrative embodiment of an inspection booth of the present invention.

DETAILED DESCRIPTION OF THE INVENTION

As shown in the drawing, a substrate 2 coated with at least one layer to be inspected is placed on a support 3 inside inspection booth 1. Typically the substrate is a glass sheet up to about four meters wide coated with a thin layer of a metal oxide such as $SnO_2$ of interferential dimensions. Support 3 is light absorbing and preferably black and, for example, is made of baize. While observation of the substrate can be made on stationary substrates, the substrates preferably are continuously moving in the direction of arrow F at speeds of up to about 20 meters per minute. To allow an observer time to evaluate the quality of a layer, it is desireable to provide an observation length of approximately three meters.

The upper part of booth 1 comprises a continuous, approximately concave surface 4, or arch, which reflects incident light onto at least a surface 5 of the substrate 2 to be inspected. Arch 4 can have the shape of a portion of a cylinder or a paraboloid and generally has a constant radius or a radius which varies in a monotonic and continuous way. Arch 4 includes an opaque, mat-type, light-diffusing surface of neutral color, similar in reflective properties to the illuminant $D_{65}$ of the ICI. The light diffusing surface should have no discontinuities or holes which would affect the uniformity of reflected light.

The arch is illuminated indirectly and uniformly by light sources 6, 7 having trichromatic coordinates near those of illuminant $D_{65}$. These light sources are surrounded on all sides except the side facing arch 4 by an enclosure 8 so as not to interfere with inspection of the substrate. The light source typically comprises rows of fluorescent tubes of the "deluxe daylight, color temperature about 6,000° K." type. Advantageously, the intensity of light sources 6,7 is adjustable so as to facilitate the observation of various types of defects, and to permit observation by various observers.

According to a preferred embodiment, observation station 9 comprises a platform situated slightly above the plane of substrate 2 (for example, about 50 cm.) and supporting at least one observer 10. The platform is positioned in the center of the line of movement F of substrate 2 such that the eye of observer 10 sees surface 5 of substrate 2 at an average angle of incidence on the order of 30°. This average angle of incidence is the angle that a line coming from the eye of observer 10 towards the center of surface 5 of substrate 2 makes with a line normal to surface 5.

Immobile substrates such as a glass plate can be observed as well as a mobile strip of glass advancing along arrow F at speeds up to approximately 20 m/min. An arch 4 of such size as to reflect light over a length on the order of three meters along arrow F will allow the observer 10 sufficient time to evaluate the quality of the substrate.

In a preferred embodiment of the invention, a reference sample 11 is provided to facilitate the evaluation of the quality of the coating of substrate 2 by observer 10. This sample 11 is placed opposite the observer, extending the entire width to be observed, on a light absorbing support, preferably black, above substrate 2, and at a position near that at which observer 10 sees substrate 2. Preferably, sample 11 is tilted so as to provide for the observer a viewing angle of incidence approximately equal to the angle of incidence for the substrate.

The side walls of booth 1, not shown in the figure, must not reflect onto the substrate to be observed. Preferably, they are vertical, of the same color as arch 4 of booth 1 and are placed close to the bounds of the width of substrate 2 to be observed. In addition, wall 12 is provided behind the observer to close the booth entirely and avoid any influence due to illumination from the environment external to the booth.

Observer 10 is preferably located in the center of platform 9 to enable him to inspect widths of substrate on the order of 2 m on each side of him.

The present invention permits the evaluation of the quality of very thin layers deposited on glass substrates, as well as the evaluation of other substrates, stationary or in linear motion, transparent or not, under conditions similar to outdoor daylight.

What is claimed is:

1. A booth for observing the quality of a substrate coated with at least one layer comprising:
   an arch extending above said substrate to be observed, said arch being a continuous, curved surface covered with an opaque, mat-type, neutral-colored, light-diffusing coating, and approximately equivalent in reflective properties to the illuminant $D_{65}$ of the I.C.I. (International Commission on Illumination),
   illuminating means with properties similar to illuminant $D_{65}$ mounted under said arch for illuminating said arch so that indirectly and uniformly light from said illuminating means is reflected towards said substrate, and
   an observation station located such that an observer situated thereon and facing toward said arch observes said substrate at an average angle of incidence of approximately 30 degees to the normal to the substrate.

2. The apparatus of claim 1 characterized in that said arch has a curvature of constant radius.

3. The apparatus of claim 1 characterized in that said arch has a curvature that varies monotonically.

4. The apparatus of claim 1 characterized in that a support upon which said substrate is placed is light absorbing.

5. The apparatus of claim 1 characterized in that an area of said substrate illuminated by light reflected from said arch is on the order of three meters long.

6. The apparatus of claim 1 characterized in that said illuminating means are of variable intensity.

7. The apparatus of claim 1 further comprising a reference sample placed opposite said observer, slightly above said substrate to be inspected, said reference sample being situated such that said observer views said reference sample with an angle of incidence approximately equal to said angle of incidence for the substrate to be inspected.

8. The apparatus of claim 1 characterized in that said observation station is approximately in the center of the width of said substrate, said substrate having a total width less than or about equal to four meters.

9. The apparatus of claim 1 characterized in that approximately vertical lateral walls of color similar to said arch are placed on both sides of said booth.

10. The apparatus of claim 1 characterized in that said booth is totally enclosed.

11. The apparatus of claim 1 characterized in that said layer is a metallic oxide.

12. The apparatus of claim 1 characterized in that said substrate is glass.

13. The apparatus of claim 1 characterized in that said substrate is immobile during inspection.

14. The apparatus of claim 1 further comprising means for moving the substrate past the observation station.

* * * * *